United States Patent
Klein et al.

[11] Patent Number: 5,395,993
[45] Date of Patent: Mar. 7, 1995

[54] PREPARATION OF ALKENOLS

[75] Inventors: Ulrich Klein, Limburgerhof; Ernst Buschmann, Ludwigshafen; Christiane Mackenroth, Bad Durkheim, all of Germany

[73] Assignee: BASF Aktiengesellschaft, Ludwigshafen, Germany

[21] Appl. No.: 191,715

[22] Filed: Feb. 4, 1994

Related U.S. Application Data

[63] Continuation of Ser. No. 994,257, Dec. 21, 1992, abandoned.

[30] Foreign Application Priority Data

Dec. 21, 1991 [DE] Germany .................. 41 42 515.4

[51] Int. Cl.$^6$ .................. C07C 29/32; C07C 33/025; C07C 33/05
[52] U.S. Cl. .................. 568/878; 568/902; 568/909.5
[58] Field of Search .................. 568/878, 902

[56] References Cited

U.S. PATENT DOCUMENTS

| | | | |
|---|---|---|---|
| 2,905,717 | 9/1959 | Sarmecki et al. | 260/606.5 |
| 3,006,939 | 10/1961 | Pommer et al. | 568/878 |
| 3,960,977 | 6/1976 | Naf et al. | 568/878 |
| 4,118,406 | 10/1978 | Bestmann et al. | 568/878 |

FOREIGN PATENT DOCUMENTS

| | | |
|---|---|---|
| 0032396 | 7/1981 | European Pat. Off. |
| 0266544 | 5/1988 | European Pat. Off. |
| 3237632 | 4/1984 | Germany |
| 4006919 | 9/1991 | Germany |

OTHER PUBLICATIONS

Chem. Abst., vol. 111, No. 13, (1980) entry 114957.
March, Advanced Organic Chemistry 2nd Ed. McGraw Hill, pp. 864–872 (1977).
Vinczer et al., OPPI Briefs, vol. 12, pp. 443–447 (1991).
Minks et al., Entomol Exp. Appl. 49:25–36 (1988).
Hendrick, Tetrahedron, 34, 1845, (1977).
Houben-Weyl, Bd. V/1b, 383 f. (1972).
Szantay et al., Acta Chim. Hung., 125,797 (1988).
Maerker et al., Org. React. 14, 402 (1965).
Okuma et al., Bull. Chem. Soc. Jpn., 61, 4476 (1988).
Hortike et al., Agric. Biol. Chem., 44(2), 257 (1980).
Schlosser et al., Tetrahedron Lett., 26, 307 (1985).
Organic Synthesis, vol. 3, 470 f. (1955).
Ohloff et al., Helv. Chim. Acta, 60, 1161 (1977).
Paul et al., Bull. Soc. Shim. Fr., (5), 1, 971 (1934).
Sonnet, Tetrahedron, 36, 557 (1980).

*Primary Examiner*—Joseph E. Evans
*Attorney, Agent, or Firm*—Keil & Weinkauf

[57] ABSTRACT

A process for preparing alkenols of the formula I $$R^1\text{—CH}=\text{CH(CH}_2)_n\text{OH} \qquad \text{I}$$

where $R^1$ is hydrogen or a hydrocarbon radical, and n is an integer from 3 to 15, a) by reacting a phosphonium salt of the formula IIa $$R^1\text{—CH}_2\text{—P}^+(C_6H_5)_3 X^- \qquad \text{IIa}$$

where X is chlorine, bromine or iodine, with an aldehyde of the formula IIIa or its hemiacetal of the formula IIIb

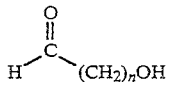

IIIa

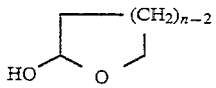

IIIb or b) by reacting a phosphonium salt of the formula IIb $$(C_6H_5)_3P^+(CH_2)_{n+1}OH\ X^- \qquad \text{IIb}$$

with a aldehyde of the formula IV $$R^1CHO \qquad \text{IV}$$

in a solvent in the presence of a base, wherein the base is the alkali metal salt of an alcohol and the solvent is an alcohol.

9 Claims, No Drawings

PREPARATION OF ALKENOLS

This application is a continuation of application Ser. No. 07/994,257, filed on Dec. 21, 1992, now abandoned.

The present invention relates to a process for preparing alkenols of the formula I $$R^1-CH=CH(CH_2)_nOH \qquad \text{I}$$

where $R^1$ is hydrogen or a hydrocarbon radical, and n is an integer from 3 to 15, a) by reacting a phosphonium salt of the formula IIa $$R^1-CH_2-P^+(C_6H_5)_3 X^- \qquad \text{IIa}$$

where X is chlorine, bromine or iodine, with an aldehyde of the formula IIIa or its hemiacetal of the formula IIIb <chemical structure: H-C(=O)-(CH2)nOH> IIIa <chemical structure: cyclic hemiacetal HO-CH-O-(CH2)n-2> IIIb or b) by reacting a phosphonium salt of the formula IIb $$(C_6H_5)_3P^+(CH_2)_{n+1}OH\ X^- \qquad \text{IIb}$$

with an aldehyde of the formula IV $$R^1CHO \qquad \text{IV}$$

in a solvent in the presence of a base, wherein the base is the alkali metal salt of an alcohol and the solvent is an alcohol.

The present invention furthermore relates to a process for preparing alkenols starting with the reaction of an alkyl halide of the formula Va or Vb $$R^1-CH_2-X \qquad \text{Va}$$

$$X-(CH_2)_{n+1}-OH \qquad \text{Vb}$$

with triphenylphosphine or starting with the reaction of an alcohol of the formula VI $$R^1-CH_2-OH \qquad \text{VI}$$

with a hydrohalic acid to give the corresponding alkyl halide of the formula Va.

The present invention additionally relates to processes for the preparation of 5-decen-1-ol starting from n-pentanol, of 4-tridecen-1-ol starting from n-nonanol, of 8-dodecen-1-ol starting from 8-bromooctan-1-ol and of 9-dodecen-1-ol starting from 9-bromononan-1-ol.

Alkenols of the formula I are important as pheromones or precursors for synthesizing pheromones. (For a review of structures, see: List of sex pheromones of Lepidoptera and related attractants, H. Arn., M. Toth and E. Priesner, OILB, 1986). They are employed as attractants in insect traps in order to detect infestation. However, only kilogram quantities are used for this world-wide, and these can be prepared by laboratory methods.

The growth in use of the method of interfering with mating with application rates of from 10 to 1000 g of pheromone per hectare and year is increasing the demand for pheromones. (A review of the use of pheromones in the method of interfering with mating is given by A. K. Minks and R. T. Cardé in Entomol. exp. appl. 49, (1988) 25-36). The methods designed for laboratory synthesis (see, for example, K. Mori, The Synthesis of insect pheromones in: The total synthesis of natural products, Volume 4, pp. 1 et seq., Wiley-Interscience, New York, 1981; C. A. Henrick, Tetrahedron 33, (1977) 1845-1889) must therefore be modified so that they can be used for the industrial synthesis of the compounds in tonne quantities.

Alkenols are currently prepared industrially in a plurality of stages with alkyne precursors (e.g. EP-A 32,396). The starting compounds are acetylene or alkynes, reaction of which represents a certain safety risk, just like the metallation steps necessary on several occasions in these syntheses.

The preparation of alkenols by the Wittig reaction has also been disclosed. Syntheses of this type take place via non-stabilized phosphonium ylides.

Wittig reactions of non-stabilized phosphonium ylides are currently carried out in solvents such as THF, dioxane, dimethylformamide, hexamethylphosphoric triamide, dimethyl sulfoxide or similar solvents (see Houben-Weyl, Methoden der Organischen Chemie, Thieme 1972, Volume V 1b, pp. 383 et seq.). These solvents have the disadvantage that on aqueous workup of the reaction mixtures, because they are hydrophilic, remain dissolved in the aqueous phase so that disposal is elaborate and costly. Solvents of this type are therefore unsuitable for economic and ecological reasons for preparation on the industrial scale.

Alternatively, it is also possible to employ hydrocarbons such as benzene, toluene, xylenes or hexane (see C. Szantay et al. Acta Chim. Hung. 125, (1988) 797). These make aqueous workup of the reaction mixtures possible, and this leads to less pollution of waste waters. However, the disadvantage is that the reaction must be carried out at great dilution so that the phosphonium salt suspension can be stirred. The space/time yields are very low.

Bases used to date are: n-butyllithium, potassium in HMPT, sodium hydride, sodium hexamethyldisilazide, as well as bases which are easier to handle and less costly such as potassium tert-butylate, sodium methylate, sodium ethylate, potassium methylate and potassium ethylate, which likewise give good yields in nonpolar solvents. Wittig reactions with stabilized ylides such as $$Ph_3P^+CH_2CO_2Et \qquad \text{IIb}$$

take place in polar protic solvents such as alcohols with good yields and are therefore widely used, including in industry.

Unstabilized ylides as are necessary for preparing the alkenols I, give on the present state of knowledge, poor yields of reaction in alcohols so that it is even recommended when alcoholate bases are used that the small amount of alcohol produced thereby be carefully removed before reacting further (C. Szantay, Acta Chim. Hung. 125 (1988) 807).

For the reasons given above, the Wittig reaction with unstabilized ylides has to date hardly been used in industry.

We have now found that alkenols of the formula I can be prepared particularly advantageously, even on the industrial scale, by reacting either a) a phosphonium salt of the formula IIa with an aldehyde of the formula IIIa or its hemiacetal of the formula IIIb or b) a phosphonium salt of the formula IIb with an aldehyde of the formula IV in a solvent in the presence of a base, using the alkali metal salt of an alcohol as base and an alcohol as solvent.

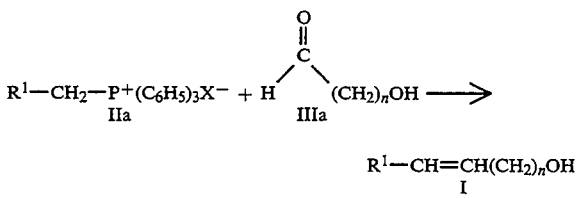

or

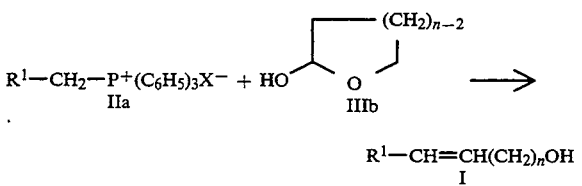

or

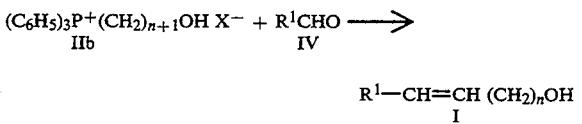

X in the formulae IIa and IIb is chlorine, bromine and iodine, preferably bromine.

n in the formulae I, IIb and IIIa or IIIb is an integer from 3 to 15.

According to current knowledge, the value of n has an influence in the reaction of hemiacetals of the formula IIIb only to the extent that 5- and 6-membered cyclic hemiacetals (n=3 or 4) are preferred because of their stability.

$R^1$ in the formulae IIa and IV is hydrogen or a hydrocarbon radical.

Suitable hydrocarbon radicals are alkyl of 1–20 carbons, preferably $C_1$–$C_{15}$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, and the corresponding unbranched or branched heptyl, octyl, nonyl, decyl, undecyl, dodecyl, tridecyl and pentadecyl radicals.

Alkenyl of 2–20 carbons, preferably $C_2$–$C_{15}$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, and the corresponding branched and unbranched heptenyl, octenyl, nonenyl, decenyl, undecenyl, dodecenyl, tridecenyl, tetradecenyl and pentadecenyl radicals.

Alkynyl of 2–20 carbons, preferably $C_2$–$C_{15}$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl, and the corresponding unbranched and branched heptynyl, octynyl, nonynyl, decynyl, undecynyl, dodecynyl, tridecynyl, tetradecynyl and pentadecynyl radicals.

Cycloalkyl of 3–17 carbons, preferably $C_3$–$C_8$-cycloalkyls such as cyclopropyl, cyclobutyl, cyclopentyl, cyclohexyl, cycloheptyl and cyclooctyl, cycloalkenyl of 5–17 carbons, preferably $C_5$–$C_8$-cycloalkenyl such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 4-cycloheptenyl, 1-cyclooctenyl, 2-cyclooctenyl, 3-cyclooctenyl and 4-cyclooctenyl, cycloalkadienyl of 5–12 carbons, preferably $C_5$–$C_8$-cycloalkadienyl such as cyclopenta-1,3-dien-1-yl, cyclopenta-1,3-dien-2-yl, cyclopenta-1,3-dien-5-yl, cyclohexa-1,3-dien-1-yl, cyclohexa-1,3-dien-2-yl, cyclohexa-1,3-dien-5-yl, cyclohexa-1,4-dien-1-yl, cyclohexa-1,4-dien-3-yl, cyclohepta-1,3-dien-1-yl, cyclohepta-1,3-dien-2-yl, cyclohepta-1,3-dien-5-yl, cyclohepta-1,3-dien-6-yl, cyclohepta-1,4-dien-1-yl, cyclohepta-1,4-dien-2-yl, cyclohepta-1,4-dien-3-yl, cyclohepta-1,4-dien-6-yl, cycloocta-1,3-dien-1-yl, cycloocta-1,3-dien-2-yl, cycloocta-1,3-dien-5-yl, cyclooc-ta-1,3-dien-6-yl, cycloocta-1,4-dien-1-yl, cycloocta-1,4-dien-2-yl, cycloocta-1,4-dien-3-yl, cycloocta-1,4-dien-6-yl, cycloocta-1,4-dien-7-yl, cycloocta-1,4-dien-1-yl and cycloocta-1,4-dien-3-yl, and aromatic systems such as phenyl and naphthyl.

These hydrocarbon radicals may in turn have substituents which are inert under the reaction conditions. Examples of such substituents are alkyl of from one to six carbons (in the case of cyclic hydrocarbons), corresponding alkoxy or alkylthio, cyclic groups as specified above, unsubstituted or substituted aromatic radicals such as, in particular, phenyl, and halogen as specified above, these substituents having, according to current knowledge, no effect on the reaction.

Hydrocarbon radicals which are particularly preferred for $R^1$ in view of the use of the synthetic products as pheromones are alkyl, alkenyl and alkynyl of 5–15 carbons.

The reactions according to the invention are carried out specifically as follows:

A: Reaction of a phosphonium salt of the formula IIa with an aldehyde of the formula IIIa or its hemiacetal of the formula IIIb

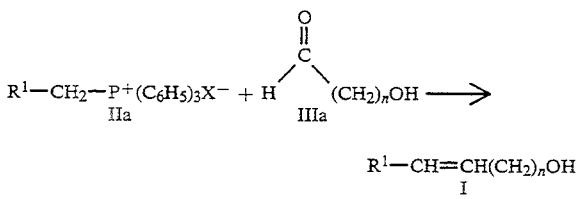

or

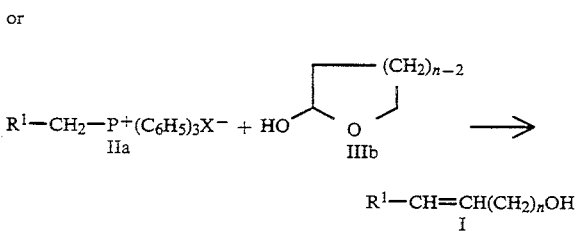

Wittig reactions are generally carried out at from 0° C. to the boiling point of the solvent. The phosphorus ylide is prepared in situ and normally then reacted with the aldehyde (see Houben-Weyl, Methoden der organischen Chemie, Thieme 1972, Volume V, 1b, pp. 383 et seq.).

The process according to the invention is generally carried out at from −50° to 150° C., preferably at from 50° to 100° C. when the aldehydes IIIa are used and preferably at from 0° to 50° C. when the aldehydes IV are used.

The solvent used according to the invention for this reaction is an alcohol, for example a $C_1$-$C_{15}$-alcohol, and the degree of branching is of importance only to the extent that the alcohol used must be liquid at the reaction temperature.

The bases preferably used are low molecular weight alkali metal alcoholates such as sodium methylate, sodium ethylate, potassium methylate, potassium ethylate, sodium tert-butylate and potassium tert-butylate. It is particularly beneficial to use alkali metal alcoholate solutions in the corresponding alcohols because this represents a simplification of the process. Examples are sodium or potassium methanolate in methanol or sodium or potassium ethanolate in ethanol. It is advantageous to remove the solvent for the alcoholate (e.g. methanol or ethanol) by distillation from the reaction mixture after addition of the base. This keeps the reaction volume small. The alcohol can be reused and does not interfere with the subsequent aqueous workup.

The bases are generally employed in at least the stoichiometric amount but they are normally used in an excess of from 10 to 150%, preferably 50 to 100%.

The precursors are generally reacted together in equimolar amounts. It may be advantageous for the yield to employ the aldehyde in an excess of from 10 to 20% relative to the phosphonium salt.

The reaction mixtures are initially diluted with water and then worked up in a conventional manner, e.g. by separating the phases and, where necessary, purifying the crude products by chromatography. The intermediates and final products are in some cases obtained in the form of colorless or pale brown viscous oils which are heated at moderately elevated temperature under reduced pressure to remove volatiles or purify. When the intermediates and final products are obtained as solids they can be purified by recrystallization or digestion.

B: Reaction of a phosphonium salt of the formula IIb with an aldehyde of the formula IV

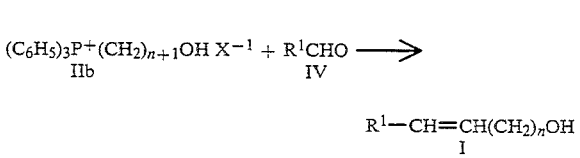

This reaction is generally carried out under the conditions described for Process A.

The starting materials required for reactions A and B can be prepared beforehand in situ in their reaction medium in a particularly straightforward manner.

Phosphonium salts of the formula IIa are obtained by reacting triphenylphosphine with suitable alkyl halides such as methyl bromide, ethyl bromide, butyl bromide, isobutyl bromide, pentyl bromide, hexylbromide and octyl, nonyl and decyl bromides. The corresponding chlorides and iodides are also suitable for this reaction. The reaction is carried out in one of the many suitable solvents such as xylene, toluene, THF, dimethoxyethane, diethoxyethane, acetonitrile, dimethyl sulfoxide, dimethylformamide and N-methylpyrrolidone at 80°–150° C., under atmospheric pressure for the higher-boiling halides and under superatmospheric pressure for lower-boiling halides. The phosphonium salts of the formula IIa are usually solids which crystallize out of the solvent on cooling. They are filtered off and employed as solids in the next stage. A review of phosphonium salts is given by A. Maercker in Org. Reactions 14 (1965) 402. It is advantageous to synthesize the phosphonium salts IIa from alcohols of the formula VI, triphenylphosphine and hydrogen halide as described in DE-A 10 46 046.

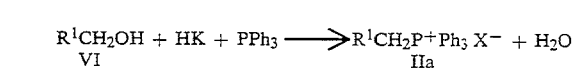

The alcohol VI can be used as solvent in this case. If the alcohol is immiscible or only slightly miscible with water, the alcoholic solution of IIa in VI can be employed in the next stage. However, the water produced in the reaction or introduced by using an aqueous solution of HX must be removed beforehand by azeotropic distillation.

Phosphonium salts of the formula IIb can be obtained from cyclic ethers (K. Okuma, Bull. Chem. Soc. Jpn. 61, (1988) 4476–4478) or from bromo alcohols of the formula Vb (see EP 266 544 for preparation) and triphenylphosphine (see, for example, M. Horiike et al. Agric. Biol. Chem. 44 (1980) 257–261), M. Schlosser et al., Tetrahedron Lett. 26 (1985) 307).

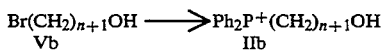

$$\underset{\text{Vb}}{\text{Br(CH}_2\text{)}_{n+1}\text{OH}} \longrightarrow \underset{\text{IIb}}{\text{Ph}_2\text{P}^+\text{(CH}_2\text{)}_{n+1}\text{OH}}$$

Examples of solvents suitable for this reaction are methanol, ethanol, acetonitrile, N-methylpyrrolidone, dimethylformamide, xylene, toluene and chlorobenzene. The reaction is carried out at from 80° to 160° C. Preferred solvents are alcohols which are immiscible or only slightly miscible with water. The phosphonium salts IIb then do not have to be isolated, it being possible to employ the solution thereof directly in the next stage.

Wittig Preparation of the Alkenols I

The phosphonium salts of the formulae IIa and IIb are dissolved or suspended in an alcohol, for example: methanol, ethanol, 1-propanol, 2-propanol, n-butanol, isobutanol, n-pentanol, 2-pentanol, 3-pentanol, 1-hexanol, 2-hexanol, 3-hexanol, 1-heptanol, 2-heptanol, 1-octanol, 1-nonanol, 3-heptanol, 2-octanol, 2-nonanol, 1-decanol, 2-methyl-2-butanol and 2-ethylhexanol.

It is more advantageous if the phosphonium salt IIa or IIb has already been prepared in a suitable alcohol as described above, so that isolation of the salt is unnecessary.

The phosphonium salts IIa and IIb in the alcoholic solution or suspension are converted with a base into the corresponding ylides and subsequently reacted with the aldehydes of the formula IIIa/IIIb or IV to give the alkenols I.

The preparation of the aldehyde of the formula IIIa (in equilibrium with its hemiacetal IIIb)

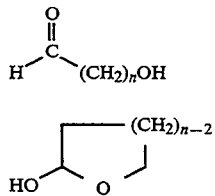

IIIa

IIIb is described for n=4 in Organic Synthesis Coll. Vol. 3, p. 470. The corresponding aldehyde with n=3 can be prepared by a similar method. (see also G. Ohloff et al. Helv. Chim. Acta 60 (1977) 1161, R. Paul and S. Tchelitcheff Bull. Soc. Chim. Fr., (5) 1 (1934) 971).

The Wittig reaction according to the invention, described above, in alcohols which are not completely miscible with water results, like other processes disclosed in the literature, in mixtures of Z and E isomers (see, for example, C. Szantay et al. Acta Chim. Hung. 125 (1988) 797–820). The proportion of the Z isomer ranges from 75 to 90%.

The advantage of using alcohols as solvents in Wittig reactions is that, because they are good solvents for the phosphonium salts, the reaction can be carried out at higher concentrations so that the space/time yields are considerably increased.

The use of alcohols which are incompletely or only slightly miscible with water has another advantage in that the waste water produced in the aqueous workup has only a small content of organic impurities and can be disposed of through a normal treatment plant.

This means that an industrially utilizable process, which is both economically and ecologically favorable, is now available for preparing alkenols.

Some of the alkenols of the formula I are important as pheromones and can thus be employed for controlling pests. Examples are: 5Z-decenol, 5Z-dodecenol, 7Z-dodecenol, 8Z-dodecenol, 9Z-dodecenol, 7Z-tetradecenol, 8Z-tetradecenol, 9Z-tetradecenol, 11Z-tetradecenol, 9Z-hexadecenol, 11Z-hexadecenol and 13Z-octadecenol.

The Z-alkenols can be isomerized to the corresponding E-alkenols (P. E. Sonnet, Tetrahedron 36 (1980) 557–604). E-alkenols and Z-alkenols can be reacted with acetylating agents (e.g. acetic anhydride) to give the corresponding acetates. Just like the Z-alkenols detailed above, E-alkenols and numerous acetates of Z- and E-alkenols are also known as pheromones and can be used in crop protection.

PREPARATION EXAMPLES

Example 1

4-Tridecenol

A mixture of 576 g (4.0 mol) of 1-nonanol, 262 g (1.0 mol) of triphenylphosphine and 173.4 g (1.1 mol) of 47% strength hydrobromic acid is heated at 100°–120° C. until about 112 ml of water have been removed azeotropically. The mixture is then stirred at 140° C. for 6 h and, after cooling to 25° C., 99 g (1.8 mol) of sodium methylate are added, when the temperature rises to about 45° C. The mixture is then stirred at 25° C. for 0.5 h. At 62° C., 110 g (1.0 mol) of 80% strength 2-hydroxytetrahydrofuran are added, when the temperature rises to 90° C. The mixture is stirred at 80° C. for 2 h and then poured into 300 ml of water. The organic phase is isolated and, after evaporation of the volatiles, is distilled to give 115 g (58%) of 4-tridecenol at 120°/0.1 mbar, E:Z isomer ratio=14:86.

Example 2

5-Decenol

A mixture of 660 g (7.5 mol) of 1-pentanol, 362 g (1.38 mol) of triphenylphosphine and 262 g (1.55 mol) of 47% strength hydrobromic acid is heated at 115°–150° C. until about 200 ml of water have been removed azeotropically. The mixture is then refluxed for 6 h. After cooling to 20° C., 446 g (2.43 mol) of 30% strength sodium methylate solution in methanol are added. The mixture is stirred at 20° C. for 0.5 h and then about 390 ml of methanol are removed by distillation at 65° C. and 1000-60 mbar. Subsequently, at 65° C., 142 g (1.39 mol) of 2-hydroxytetrahydropyran are added dropwise. The mixture is then stirred at 80° C. for 2 h and poured into 300 ml of water. The organic phase is isolated and distilled to give 179 g (83%) of 5-decenol of boiling point 77° C./0.02 mbar, E:Z isomer ratio=19:81.

Example 3

5-Decenol

A mixture of 453 kg (1.73 kmol) of triphenylphosphine, 697 kg (7.92 kmol) of 1-pentanol and 328 kg (1.90 kmol) of 47% strength HBr is refluxed until about 200 kg of water have been removed azeotropically and is then refluxed further for 6 h. After cooling to 20°–25° C., 171 kg (3.11 kmol) of sodium methylate are added a little at a time. The mixture is stirred at 20°–25° C. for 30 min and then heated to 65° C., 177 kg (1.73 kmol) of 2-hydroxytetrahydropyran are run in at 80° C. and the mixture is stirred at 30°–80° C. for 2 hours. It is cooled to room temperature, and 300 l of water are run in. The organic phase is distilled to give 216 kg of 5-decenol (80.0%), E:Z isomer ratio = 15:85.

Example 4

8-Dodecenol

A mixture of 335.4 g (1.28 mol) of triphenylphosphine, 266.6 g (1.0 mol) of 78% pure 8-bromo-1-octanol and 450 ml of 1-pentanol is stirred at 110° C. for 5 h. After cooling to 20° C. 140 g (2.6 mol) of sodium methylate are added, when the temperature rises to 60° C. The mixture is stirred for 2 h and 92.3 g (1.28 mol) of butyraldehyde are added dropwise. The mixture is stirred at 20° C. for 12 h and then poured into 350 ml of water, and the organic phase is isolated. Distillation yields 89 g (48%) of 8-dodecenol, boiling point 98°–100°/1 mbar.

Example 5

8-Dodecenol

A solution of 335.4 g (1.28 mol) of triphenylphosphine and 240.5g (1.0 mol) of 8-bromooctanol (86.9% pure) in 400 ml of 2-butanol is refluxed for 8 h and then allowed to cool, and 140 g (2.6 mol) of sodium methylate are added a little at a time, keeping the temperature below 40° C. by cooling. The mixture is then stirred for one hour and 92.3 g (1.28 mol) of n-butyraldehyde are added dropwise at <20° C. After the mixture has been stirred at room temperature for 2 h, 350 ml of water are added. Distillation of the organic phase yields 117.4 g of 8-dodecenol (64% yield). E:Z=16:84.

We claim:
1. A process for preparing alkenols of the formula I

$$R^1-CH=CH(CH_2)_nOH \qquad I$$

where $R^1$ is hydrogen or an alkyl of 1–20 carbons or a cycloalkyl of 3–17 carbons, and n is an integer from 3 to 15, a) by reacting a phosphonium salt of the formula IIa $$R^1-CH_2-P^+(C_6H_5)_3X^- \qquad IIa$$

where X is chlorine, bromine or iodine, with an aldehyde of the formula IIIa or its hemiacetal of the formula IIIb $$\underset{H}{\overset{O}{\underset{\|}{C}}}\diagdown (CH_2)_nOH \qquad IIIa$$

$$HO\diagup\underset{O}{\diagdown}(CH_2)_{n-2} \qquad IIIb$$

or b) by reacting a phosphonium salt of the formula IIb $$(C_6H_5)_3P^+(CH_2)_{n+1}OH\ X^- \qquad IIb$$

with an aldehyde of the formula IV $$R^1CHO \qquad IV$$

in a solvent in the presence of a base, wherein the base is the alkali metal salt of an alcohol and the solvent is an alcohol.

2. A process for preparing alkenols of the formula I as claimed in claim 1, by reacting an alkyl halide of the formula Va or Vb $$R^1-CH_2-X \qquad Va$$

$$X-(CH_2)_{n+1}-OH \qquad Vb$$

with triphenylphosphine and subsequently condensing the phosphonium salt of the formula IIa or IIb defined in claim 1, which is formed, with an aldehyde of the formula IIIa or its hemiacetal of the formula IIIb or with an aldehyde of the formula IV defined in claim 1 in the presence of a base, wherein this sequence of reactions is carried out without isolating the intermediates in an alcohol as solvent.

3. A process for preparing alkenols of the formula I as claimed in claim 1, by reacting an alcohol of the formula VI $$R^1-CH_2-OH \qquad VI$$

with a hydrohalic acid to give the corresponding alkyl halide of the formula Va defined in claim 2, subsequently reacting Va with triphenylphosphine to give the phosphonium salt of the formula IIa defined in claim 1 and condensing the phosphonium salt of the formula IIa with an aldehyde of the formula IIIa or its hemiacetal of the formula IIIb defined in claim 1 in the presence of a base, wherein this sequence of reactions is carried out without isolating the intermediates in alcohol VI as solvent.

4. A process for preparing 5-decen-1-ol by reacting n-pentanol with a hydrohalic acid to give the corresponding pentyl halide, subsequently reacting the pentyl halide with triphenylphosphine to give the corresponding pentyltriphenylphosphonium salt and condensing the phosphonium salt with 5-hydroxypentanal or 2-hydroxytetrahydropyran in the presence of a base, wherein this sequence of reactions is carried out without isolating the intermediates in n-pentanol as solvent.

5. A process for preparing 4-tridecen-1-ol by reacting n-nonanol with a hydrohalic acid to give the corresponding nonyl halide, subsequently reacting the nonyl halide with triphenylphosphine to give the corresponding nonyltriphenylphosphonium salt and condensing the phosphonium salt with 4-hydroxybutanal or 2-hydroxytetrahydrofuran in the presence of a base, wherein this sequence of reactions is carried out without isolating the intermediates in n-nonanol as solvent.

6. A process for preparing 8-dodecen-1-ol by reacting 8-bromooctan-1-ol with triphenylphosphine and subsequently condensing the phosphonium salt which is formed with butyraldehyde in the presence of a base, wherein this sequence of reactions is carried out without isolating the intermediates in an alcohol as solvent.

7. A process for preparing 9-dodecen-1-ol by reacting 9-bromononan-1-ol with triphenylphosphine and subsequently condensing the phosphonium salt which is formed with propionaldehyde in the presence of a base, wherein this sequence of reactions is carried out without isolating the intermediates in an alcohol as solvent.

8. A process for preparing alkenols of the formula I $$R^1-CH=CH(CH_2)_nOH \qquad I$$

where $R^1$ is hydrogen or an alkyl of 1–20 carbons or a cycloalkyl of 3–17 carbons, and n is an integer from 3 to 15, by reacting a phosphonium salt of the formula IIA $$R^1-CH_2-P^+(C_6H_5)_3X^- \qquad IIa$$

where X is chlorine, bromine or iodine, with an aldehyde of the formula IIIA or its hemiacetal of the formula IIIB

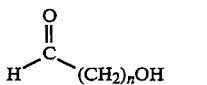  IIIa

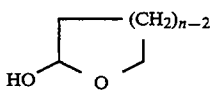  IIIb in a solvent in the presence of a base, wherein the base is the alkali metal salt of an alcohol and the solvent is an alcohol.

9. A process for preparing alkenols of the formula I $$R^1-CH=CH(CH_2)_nOH \qquad I$$

where $R^1$ is hydrogen or an alkyl of 1–20 carbons or a cycloalkyl of 3–17 carbons, and n is an integer from 3 to 15, by reacting a phosphonium salt of the formula IIb $$(C_6H_5)_3P^+(CH_2)_{n+1}OH\ X^- \qquad IIb$$

with an aldehyde of the formula IV $$R^1CHO \qquad IV$$

in a solvent in the presence of a base, wherein the base, wherein the base is the alkali metal salt of an alcohol and the solvent is an alcohol.

* * * * *